United States Patent [19]

Timmer et al.

[11] Patent Number: 4,831,170

[45] Date of Patent: May 16, 1989

[54] PHARMACEUTICALLY ACTIVE PHOSPINO-HYDROCARBON-GROUP VIII-METAL COMPLEXES, ANTITUMOR COMPOSITIONS CONTAINING THESE COMPLEXES, AND A PROCESS FOR PREPARING SAID COMPOUNDS OR ANTITUMOR COMPOSITIONS

[75] Inventors: Klaas Timmer, Bilthoven; Harmen A. Meinema, Leusden, both of Netherlands; E. Schurig, Killingworth, Conn.

[73] Assignee: Nedenlandse Centrale Organisatie voor Toegepart-Natuurwetenschappelijk Onderzoek, Hague, Netherlands

[21] Appl. No.: 922,655

[22] Filed: Oct. 24, 1986

[30] Foreign Application Priority Data

Oct. 25, 1985 [NL] Netherlands .................. 8502929

[51] Int. Cl.$^4$ .................. C07F 9/50; C07F 15/04; C07F 15/06; C07F 15/00
[52] U.S. Cl. .................................. 556/21; 556/18
[58] Field of Search .............. 556/18, 21; 514/501, 514/492, 502, 75

[56] References Cited

U.S. PATENT DOCUMENTS

| | | | |
|---|---|---|---|
| 3,084,179 | 4/1963 | Chatt et al. | 556/18 |
| 3,345,392 | 10/1967 | Graypon et al. | 556/18 |
| 3,428,661 | 2/1969 | Taylor | 556/18 X |
| 3,798,241 | 3/1974 | Kagan | 556/18 X |
| 3,939,188 | 2/1976 | McVicker | 556/18 X |
| 3,954,821 | 5/1976 | Herskovitz et al. | 556/18 X |
| 4,268,454 | 5/1981 | Pez et al. | 556/18 X |
| 4,302,401 | 11/1981 | Oswald | 556/18 X |
| 4,397,787 | 8/1983 | Riley | 556/18 |

FOREIGN PATENT DOCUMENTS 164970  12/1985  European Pat. Off. .............. 556/18

OTHER PUBLICATIONS

Reviews in Inorganic Chemistry, vol. 3, pp. 291-351 (1981).
Inorganic Nuc. Chem. Letters, vol. 9, pp. 1201-1205 (1973).
Journal of the Chemical Society, Part III, 1965, pp. 3060-3067, The Chemical Society, London, GB; A. D. Westland: "Five-co-ordinate palladium (II) and platinum (II)".
Journal of the Chemical Society, 1970 (A) pp. 2539-2544, The Chemical Society, London, G. B.; M. C. Hall et al: "Structure and Reactivity in Complexes of Iridium and Rhodium. Part I. Crystal and molecular structure of Bis-[1,2-bis(diphenylphosphino)-ethane]rhodium(I) perchlorate".
Chemical Abstracts, vol. 79, no. 24, Dec. 17, 1973, p. 377, summary 142424w, Columbus, Ohio, U.S.: W. Levason et al: "Potential anticancer agents. Diphenylphosphine complexes of platinum (II)", & Inorg. Nucl. Chem. Lett. 1973, 9(11) 1201-5.

*Primary Examiner*—Paul F. Shaver
*Attorney, Agent, or Firm*—Cushman, Darby & Cushman

[57] ABSTRACT

Novel bis[bis(diphenylphosphino)hydrocarbon] and bis[diphenylphosphino-diphenylarsino)hydrocarbon]-group VIII metal compounds of the formula 1 of the formula sheet, wherein $D_1 = D_2 =$ phosphorus or $D_1 =$ phosphorus and $D_2 =$ arsenic;

$A = (CH_2)_2$ or cis-CH=CH;

$X_1 = X_2$ (both if present) = halo or nitrato or $X_1 + X =$ peroxo;

Y (if present) = halide, nitrate, perchlorate, triflate or tetrahaloferrate (III) p1 n=0, 1 or 2;

M = Fe(II) Fe(III), Co(II) Rh(I) , Rh(III), Ir(I), Ir(III), Ni(II) or Pd(II), showing a tumor cell growth-inhibiting activity, novel pharmaceutical compositions containing said compounds and a method for treating tumor cells, sensitive to said compounds.

23 Claims, 8 Drawing Sheets

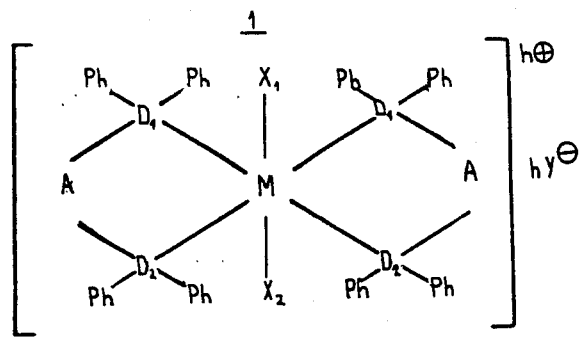
1
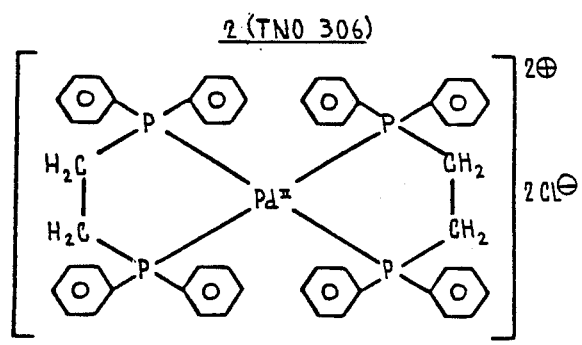
2 (TNO 306)
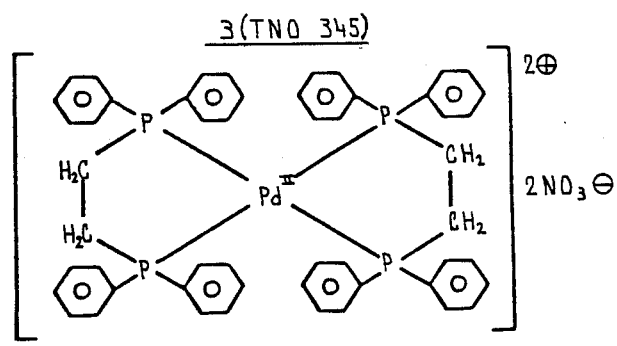
3 (TNO 345)

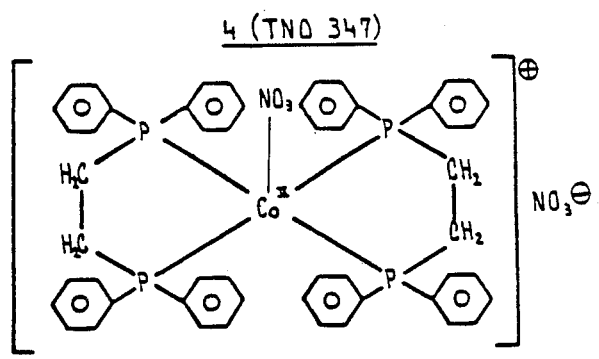
4 (TNO 347)
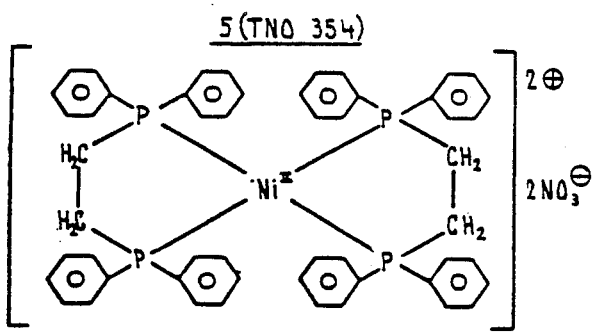
5 (TNO 354)
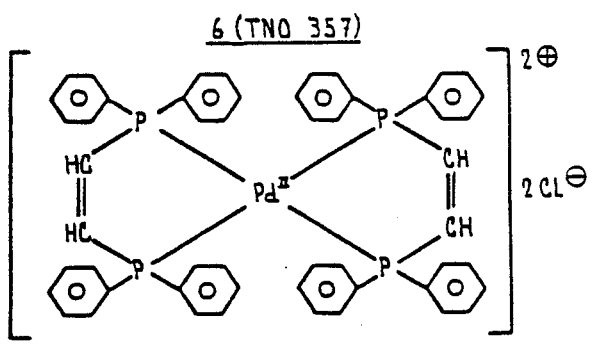
6 (TNO 357)

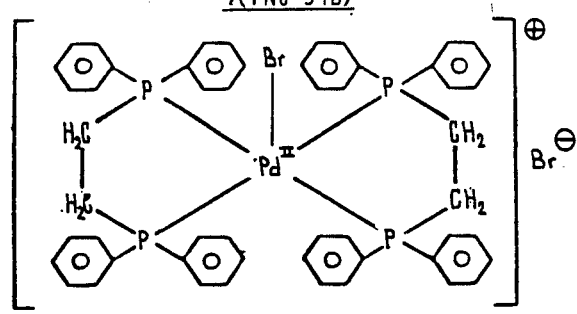
7(TNO 376)
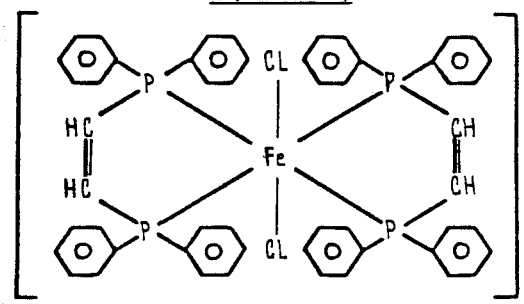
8(TNO 396)
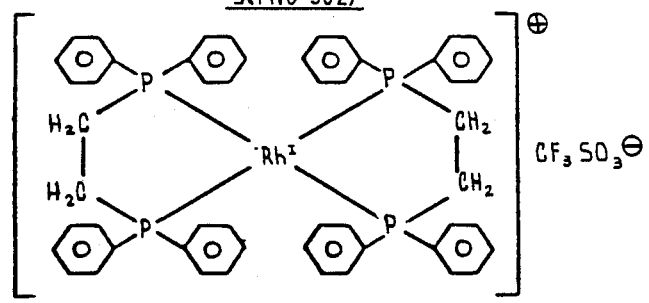
9(TNO 302)

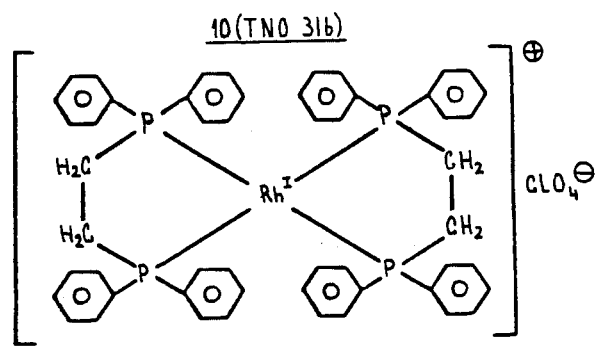
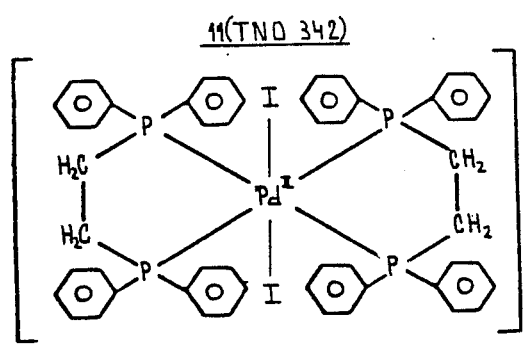
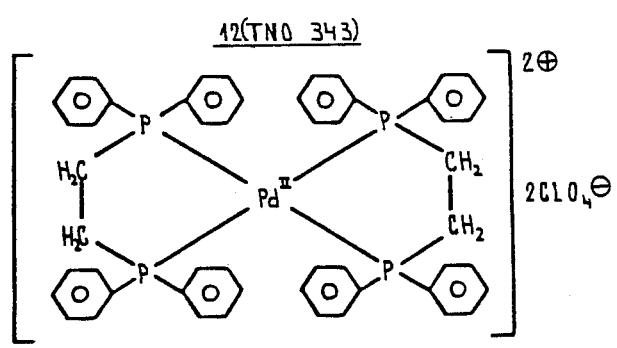

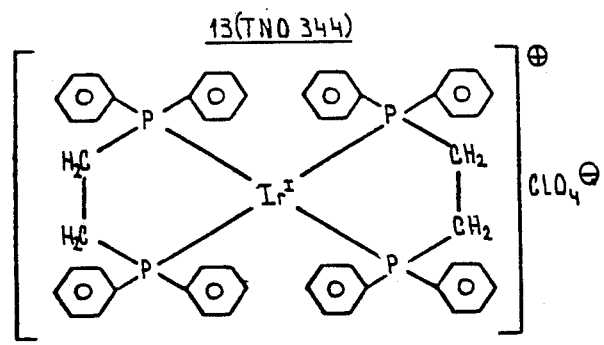
13(TNO 344)
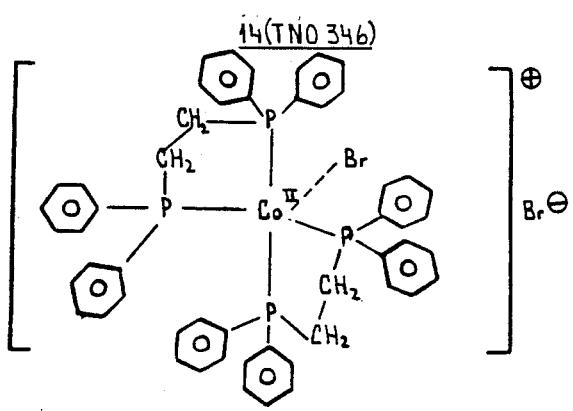
14(TNO 346)
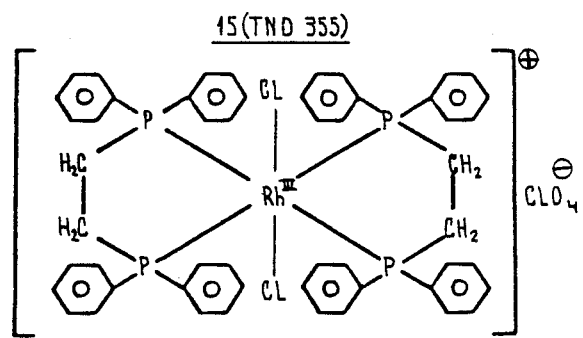
15(TNO 355)

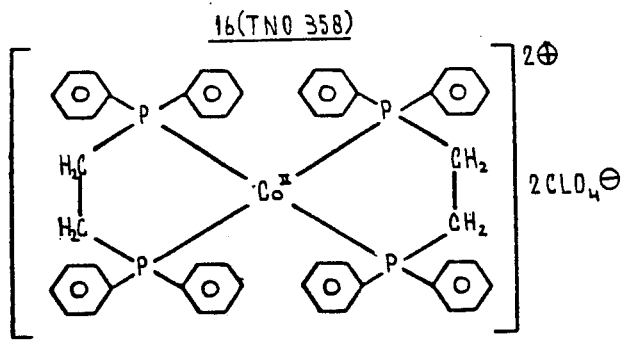
16(TNO 358)
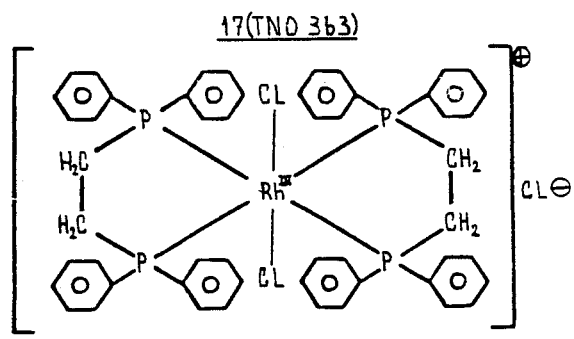
17(TNO 363)
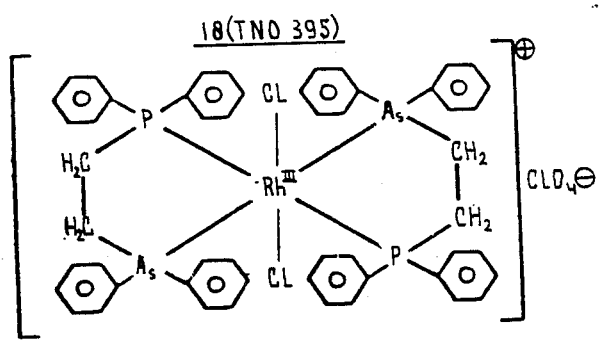
18(TNO 395)

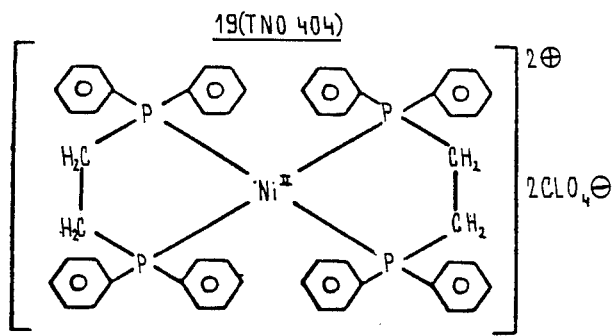
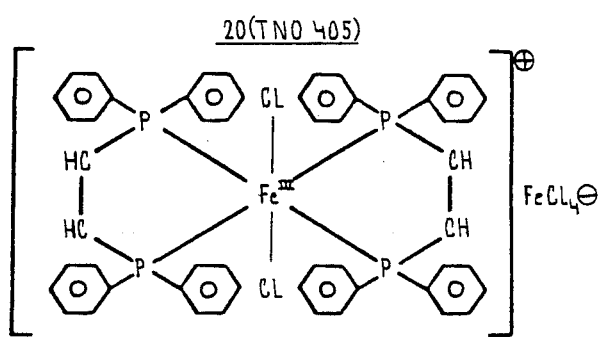
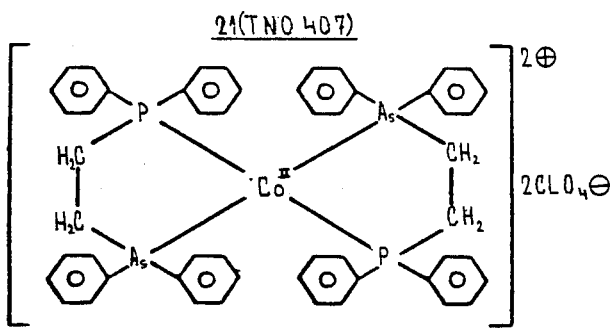

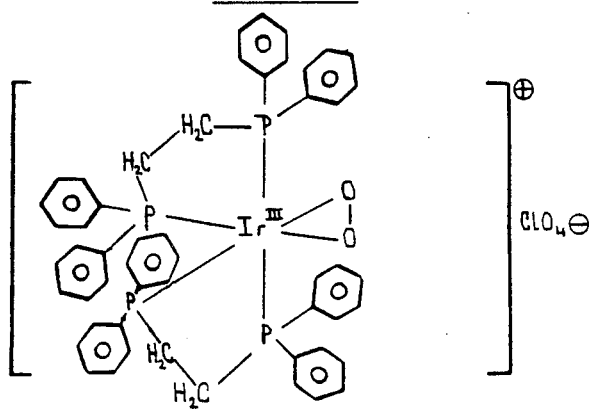
22(TNO) 413
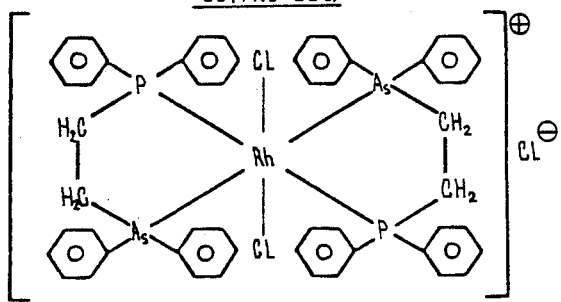
23(TNO 389)

PHARMACEUTICALLY ACTIVE PHOSPINO-HYDROCARBON-GROUP VIII-METAL COMPLEXES, ANTITUMOR COMPOSITIONS CONTAINING THESE COMPLEXES, AND A PROCESS FOR PREPARING SAID COMPOUNDS OR ANTITUMOR COMPOSITIONS

BACKGROUND OF THE INVENTION

The present invention relates to novel bis[bis(diphenylphosphino)hydrocarbon]- and bis[diphenylphosphinodiphenylarsino)hydrocarbon]-group VIII metal compounds, which have tumor cell growth-inhibiting activity, novel pharmaceutical compositions containing tumor cell growth-inhibiting amounts of such compounds and a method for treating tumor cells sensitive to such compounds by administering tumor cell growth-inhibiting amounts of such compounds to a host animal afflicted by such tumor cells.

Group VIII-transition metal complexes, especially diamminoplatinum dichloride and its use for the treatment of several types of cancer, for example testis and ovarium carcinomes, have been described by:

M. J. Cleare and P. C. Hydes, Metal Ions in Biological Systems, Vol. 11.

H. Sigel Edit., Marcel Dekker, New York (1980), 1–62 and

S. Haghighi and C. A. McAuliffe, Rev. Inorg. Chem., 3, 291–351 (1981).

Further research have been made to cis-diamminoplatinum dichloride related metal-amine complexes. Said compounds do not show activity in several antitumor test systems in mice or show a diminished activity with respect to active platinum compounds.

Metal complexes of non-nitrogeneous ligand systems have scarely been studied and, except for the phosphino-hydrocarbon-group IB-metal complexes that will be mentioned later, none of these exhibit a remarkable antitumor activity [S. Haghighi and C. A. McAuliffe, Rev. Inorg. Chem., 3, 219–351 (1981)].

There still exists a strong need for new chemotherapeutica for the treatment of cancer.

This type of chemotherapeutica should show a higher activity against certain tumors or an activity against a broader spectrum of tumors. It is of further importance that such a compound is capable of overcoming the resistance to existing antitumor chemotherapeutica.

Now, pharmaceutical active compounds of the formula 1 have been found, wherein:

$D_1 = D_2 =$ phosphorus or $D_1 =$ phosphorus and $D_2 =$ arsenic;

$A = (CH_2)_2$, $(CH_2)_3$ or cis-$CH = CH$;

$X_1 = X_2$ (both if present)=halo or nitrato or $X_1 + X_2 =$ peroxo;

Y (if present)=halide, nitrate, perchlorate, triflate or tetrahaloferrate (III);

$n = 0$, 1 or 2;

M= Fe(II), Fe(III), Co(II), Rh(I), Rh(III), Ir(I), Ir(III), Ni(II) or Pd(II).

Such nitrogen free metal complexes exhibit an important antitumor activity. They show surprising good results against P388 lymphocytic leukemia and B16 melanoma. Especially the high activity against B16 melanoma is remarkable.

The activity found is particularly unexpected, since most of the compounds are cationogenic and the corresponding cationogenic amino-platinum complexes are known to show no antitumor activity.

In this context reference is made to Nelson et al., J. Chem. Soc., Dalton Trans., 1778 (1975), disclosing bis[cis-1,2-bis-(diphenylphosphino)ethylene] dichloro iron-(II) and bis[cis-1,2-bis -(diphenylphoshino)ethylene] dichloro iron(III) tetrachloroferrate(III). Sacconi et al., Inorg. Chem., 20, 3423 (1981), disclose the X-ray crystal structure of the above mentioned iron(II) complex. Chatt et al., J. Chem. Soc., 5504 (1961), disclose bis[1,2-bis-(diphenyl phosphino)ethane] bromo cobalt(II) bromide. Sacco et al. Gazz. Chim. Ital., 93, 687 (1963), disclose several bis [1,2-bis-(diphenyl phosphino) ethane] cobalt(II) complexes (among others, bromide, iodide, perchlorate, nitrate) and bis[1,2-bis(diphenylphosphino)ethane] nickel(II) diperchlorate. Schmid et al., Z. Naturforsch. 20b, 1008 (1965), disclose bis[1,2-bis(diphenylphosphino)-ethane] chloro cobalt(II) chloride. Sacco et al., J. Chem. Soc., 3274 (1964), disclose bis[1,2-bis(diphenylphosphino)ethane] rhodium(I) chloride and its perchlorate and tetraphenylborate analogs. Arnold et al., Chem. Phys. Lett., 19, 546 (1973), disclose bis[1,2-bis(diphenyl phosphino)ethane] dichloro rhodium(III) chloride. Hieber et al., Chem. Ber., 99, 2607 (1966), disclose bis[1,2-bis(diphenylphosphino) ethane] iridium(I) chloride. Sacco et al., J. Chem. Soc. Chem. Comm., 589 (1966), disclose several bis[1,2-bis(diphenylphosphino) ethane] iridium(I) complexes (chloride, bromide, iodide, perchlorate) and bis[1,2-bis(diphenylphosphino)ethane] peroxo iridium(III) perchlorate. This last compound is described in more detail by G. Rouschias et al., J. Chem. Soc., Dalton Trans., 2531 (1974). Chatt et al., J. Chem. Soc., 2537 (1962), disclose bis[1,2-bis(diphenylphosphino)ethane] nickel(II) dinitrate and bis[1,2-bis(phenylphosphino)ethane] palladium(II) dibromide. Feltham et al., J. Chem. Soc., 4587 (1964), disclose bis[1,2-bis(diphenylphosphino)ethane] palladium(II) diperchlorate. Westland, J. Chem. Soc. A., 3060 (1965), discloses several bis[1,2-bis(diphenylphosphino)ethane] palladium(II) complexes (chloride, bromide, iodide, perchlorate). Struck et al., J. Med. Chem., 9, 414 (1966) disclos cytotoxic activity for 1,2-bis-(diphenylphosphino)ethane which is used as a starting material to prepare most of the active ingredients of the pharmaceutical compositions and methods of treatment of the subject invention.

None of the aforementioned references disclose or suggest the pharmaceutical compositions or methods of treatment of the instant invention.

Hill, Johnson and Mirabelli disclose in European patent application Nr. 0 151 046 (date of filing 31.01.1985) antitumor pharmaceutical compositions and compounds for treating tumors employing [alpha-omega-bis(disubstituted phosphino)-hydrocarbon] digold(I), digold(III), disilver(I) and dicopper(I) derivatives.

Furthermore, Berners-Price, Mirabelli, Johnson and Sadler disclose in European patent application 0 164 970 (date of filing 31.05.1985) pharmaceutical compositions, containing [bis[bis(diphenylphosphino)hydrocarbon]-, [bis[bis(diethylphosphino) hydrocarbon]- and bis[(diphenylphosphino-diethylphosphino) hydrocarbon], gold(I), silver(I) or copper(I) complexes or a tris-[bis(diphenylphosphino)ethane] dicopper(I) complex.

However, there is no disclosure or suggestion in these references of group VIII metal complexes, or that they would display cytotoxic or any other pharmaceutical activity.

Not all the compounds falling within the general formula 1 are accessible. Compound [NiCl(diphos)$_2$]$^+$Cl$^-$ can not be synthesized for instance [see R. Morassi and A. Dei, Inorg. Chim. Acta, 6, 314 (1972)].

It is further observed, that some combinations do not occur, due to reasons well known to the person skilled in the coordination chemistry, for instance when the metal is Pd(II) and the anion is Cl$^-$, there is a 4-coordination and X$_1$ and X$_2$ do not occur. When the anion is Br$^-$, 1X and 1Y can occur (5-coordination), when the anion is I$^-$, 2X occur and no Y occurs (6-coordination), when the anion is ClO$_4^-$, X does not occur and there are two Y (4-coordination). However, the possibilities will be clear to anyone skilled in this field of the art.

DETAILED DESCRIPTION OF THE INVENTION

The present invention thus especially provides compounds of the formula 1, wherein $D_1=D_2=$phosphorus or $D_1=$phosphorus and $D_2=$arsenic;

A=(CH$_2$)$_2$ or cis-CH=CH or (CH$_2$)$_3$;

X$_1$=X$_2$ (both if present)=halo or nitrato or X$_1$+X$_2$=peroxo;

Y (if present)=halide, nitrate, perchlorate, triflate or tetrahaloferrate(III);

n=0, 1 or 2;

M= Fe(II), Fe(III), Co(II), Rh(I), Rh(III), Ir(I), Ir(III), Ni(II) or Pd(II); provided that when M=Fe(II), D$_1$=D$_2$=phosphorus, A=cis-CH=CH, X$_1$=X$_2$=halo and n=0; and further provided that when M=Fe(III), D$_1$=D$_2$=phosphorus, A=cis-CH=CH, X$_1$=X$_2$=halo and Y=tetrahaloferrate(III); and further provided that when M=Co(II), D$_1$=D$_2$=phosphorus or D$_1$=phosphorus and D$_2$=arsenic, A=(CH$_2$)$_2$ or cis-CH=CH, X$_1$=halo or nitrato, n=1 and Y=halide, nitrate, perchlorate or triflate or n=2 and Y=perchlorate or triflate; and further provided that when M=Rh(I) or Ir(I), D$_1$=D$_2$=phosphorus, A=(CH$_2$)$_2$ or cis-CH=CH, n=1 and Y=chloride, nitrate, perchlorate or triflate or X$_1$=bromo or iodide and n=0; and further provided that when M=Rh(III) or Ir(III), D$_1$=D$_2$=phosphorus or D$_1$=phosphorus and D$_2$=arsenic, A=(CH$_2$)$_2$ or cis-CH=CH, X$_1$=X$_2$=halo or X$_1$+X$_2$=peroxo, n=1 and Y=halide, nitrate, perchlorate or triflate; and further provided that when M=Ni(II), D$_1$=D$_2$=phosphorus or D$_1$=phosphorus and D$_2$=arsenic, A=(CH$_2$)$_2$ or cis-CH=CH, X$_1$=bromo or iodo, n=1 and Y=bromide, iodide, nitrate, perchlorate or triflate or n=2 and Y=nitrate, perchlorate or triflate; and further provided that when M=Pd(II), D$_1$=D$_2$=phosphorus or D$_1$=phosphorus and D$_2$=arsenic, A=(CH$_2$)$_2$ or cis-CH=CH, X$_1$=X$_2$=iodo and n=0, or X$_1$=bromo, n=1 and Y=bromide, nitrate, perchlorate or triflate or n=2 and Y=chloride, nitrate, perchlorate or triflate.

The active compounds of the above mentioned formulae are either known or are prepared by methods readily available to one skilled in this art. Unless stated otherwise, the starting materials necessary to prepare the compounds are available from commercial sources. 1,2-bis(diphenylphosphino)ethane will be defined as diphos, 1-diphenylphosphino-2-diphenylarsino ethane as arphos and cis-1,2-bis (diphenylphosphino)ethylene as dppen.

The formulae noted herein are set forth in the accompanying drawings for purposes of illustration.

To prepare the iron(II) complexes, 2 mole equivalents of dppen are reacted with 1 mole equivalent or iron(II) halides in ethanol at an elevated temperature up to reflux temperature. The iron(III) complexes can be prepared by reaction of 1 mole equivalent of dppen with 1 mole equivalent of iron(III) halides in a mixture of ethanol and acetone at 70° C.

To obtain the cobalt(II) complexes, 2 mole equivalents of the appropriate ligand are reacted with 1 mole equivalent of the appropriate cobalt(II) salt, selected to provide the desired covalently bonded inorganic group X and anion(s) Y; the reactions are carried out in ethanol at reflux temperature (X=Y=halide) or in acetone at room temperature (for example X=Y=nitrate and Y=2perchlorate).

To prepare the rhodium(I) complexes, several methods to one skilled in this art are available, for example by first synthesizing the starting material (cis,cis-1,5-cyclooctadiene) rhodium(I) acetylacetonate from (cis,-cis-1,5-cyclooctadiene) chloro rhodium(I) dimer, acetylacetone and potassiumhydroxide in diethylether at -70° C. up to room temperature; 1 mole equivalent of this product can then be reacted with 1 mole equivalent of 70% perchloric acid and 2 mole equivalents of the appropriate ligand (diphos or dppen) in tetrahydrofuran at boiling temperature to obtain the complexes with Y=perchlorate. The rhodium(I) complexes with Y=triflate can be prepared by reaction of 1 mole equivalent of (cis,cis-1,5-cyclooctadiene)chloro rhodium(I) dimer with 2 mole equivalents of silvertriflate in acetone and, after removal of the formed silverchloride, with 2 mole equivalents of the appropriate ligand (diphos or dppen).

To obtain the rhodium(III) and iridium(III) complexes, 1 mole equivalent of a rhodium(III) or iridium(III) halide is reacted with 2 mole equivalents of the appropriate ligand in ethanol at reflux temperature; this reaction affords the compounds with X$_1$=X$_2$=Y=halide, which can be converted to the complexes with X$_1$=X$_2$=halo and for example Y= perchlorate by dissolving them in a mixture of ethanol and water, followed by treating with excess sodium perchlorate.

The iridium(I) complexes can be prepared by methods known to one skilled in this art, for example from 4 mole equivalents of the appropriate ligand (diphos or dppen) and 1 mole equivalent of (cis,cis-1,5-cyclooctadiene) chloro iridium(I) dimer in benzene at reflux temperature; the compound thus obtained with Y= chloride can be converted to the analogs, for example with Y= perchlorate, by dissolving in methanol and precipitation with excess sodiumperchlorate.

Both the iridium(I) and rhodium(I) complexes can easily be converted to the metal(III) analogs with X$_1$+X$_2$= peroxo by reaction with air-oxygen in dichloromethane at room temperature.

To obtain the nickel(II) complexes, 2 mole equivalents of the appropriate ligand are reacted with 1 mole equivalent of the appropriate nickel(II) salt; the reactions are carried out in a mixture of ethanol and water and boiling temperature (X=Y=halo, other than chloro or Y=2 nitrate) or in acetone at room temperature (Y=2 perchlorate).

The palladium(II) complex with Y=2 chloride can be prepared by reaction of bis-(acetonitrile) dichloro palladium(II) with 1 mole equivalent of the appropriate ligand in benzene at reflux temperature, followed by reaction with a second equivalent of ligand in dimethylformamide at 80° C. This compound can be converted to the analog, for example with Y= perchlorate, by dissolving in a mixture of ethanol and water, followed by precipitation with excess dilute perchloric acid or to the anolog with $X_1+X_2=$ iodide by dissolving in a mixture of ethanol and water, followed by adding this solution to a solution of excess sodium iodide in water at room temperature.

This invention also relates to a pharmaceutical composition which comprises an effective tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of the above mentioned formula.

IN VITRO CYTOTOXICITY

The cytotoxic activity of the metal complexes was evaluated in vitro using B16-F10 murine melanoma cells and HCT-116 human colon carcinoma cells. The B16-F10 cell line was maintained in culture in Eagle's Minimum Essential Medium (MEM) with Earle's salts (Gibco) enriched with 2 mM L-glutamine, 2.06 mM sodium pyruvate, insulin (0.26 units/ml), penicillin/-streptomycin (100 units/ml and 100/ug/ml, respectively), MEM non-essential amino acids (0.6% Gibco) and 10% fetal bovine serum (Hyclone). The HCT-116 cells were grown in McCoy's 5A medium (modified, Gibco) supplemented with 2mM L-glutamine, 0.12 mM L-serine, 0.17 mM asparagine, 1.5 mM sodium pyruvate, MEM essential amino acids (0.625%, Gibco), MEM non-essential amino acids (0.67%, Gibco), MEM vitamins (0.6%, Gibco), fetal calf serum (10%, Hyclone) and penicillin/streptomycin (100 units/ml and 100/μg/ml, respectively). Both cell lines were incubated at 37° C. in 5% $CO_2$/balance air high-humidity incubator.

Logarithmically growing cells were harvested by mild trypsinization and 4000 cells were added to each well of a 96-well microtiter plate (Costar). The plates were incubated at 37° C. in 5% $CO_2$ overnight to permit cell attachment to the plate. The cells were then treated with a metal complex or cisplatin and incubated for 72 hours. The plates were inverted and shaken to remove media, drug and detached cells. Formalin (10%) in phosphate buffered saline was added and the cells fixed for 10 minutes. The fixative was removed, the plates air dried, stained with 0.0075% crystal violet for 15 minutes, washed twice and air dried. The stain was solubilized with 0.2 ml of 0.1 M AcOH/EtOH (1:1) and optical densities determined using a Dynatech MR600 microtiter plate reader. IC50 valves were calculated by linear regression analysis of absorption data.

The results of the in vitro cytotoxicity testing of several compounds are shown in Table I.

ACTIVITY AGAINST MURINE LEUKEMIAS

All of the metal complexes were tested for antitumor activity against P388 murine leukemia. Selected compounds were also tested for antitumor activity against L1210 murine leukemia and a subline of L1210 murine leukemia resistant to cisplatin (L1210:DDP). $CDF_1$ mice weighing 20 grams were inoculated intraperitoneally with $10^6$ ascites cells of P388 leukemia, L1210 leukemia or L1210:DDP leukemia, depending on the test system being used. Drug administration was initiated the day following tumor implantation in all test systems. The complexes were administered at various dose levels by intraperitoneal injection. Groups of four to six mice were used for each dose level and they were treated with the complex on day one only. A group of ten saline treated control mice was included in each experiment. Cisplatin treated groups were included as a positive control in each experiment. The mice were weighed before treatment and again on day five or six and the average weight change used as a measure of toxicity. The animals were observed daily for mortality and the experiments terminated after 30 days. Antitumor activity was determined based on % T/C, which is the ratio of the median survival time of the drug treated group to the median survival time of the saline treated control group times 100. The saline treated mice usually have a median survival time of 9 days with P388 leukemia and 7 days with L1210 and L1210/DDP leukemia. A complex is considered active if it produces a % T/C of ≧125.

Tables II and IIa contain summaries of the evaluations of the compounds for antitumor activity against the murine leukemias. Listed for each compound is the maximum % T/C achieved and the dose producing that effect.

ACTIVITY AGINST B16 MELANOMA

Several of the metal complexes were additionally evaluated for antitumor activity against B16 Melanoma. $BDF_1$ mice, 10 per group, were inoculated intraperitoneally with 0.5 ml of a 10 percent (w:v) brei of B16 Melanoma. Intraperitoneal treatment with the metal complexes was initiated one day after implant and continued daily for a total of nine days. From 4 to 5 doses were tested for each compound under study. A saline treated control group and cisplatin treated groups were included in each experiment. The mice were observed daily for survivors and the experiments terminated after 60 days. The saline treated control mice exhibited a median survival time of 20–26 days. The median survival time of the drug treated mice relative to that of the controls (% T/C) was used as a measure of antitumor activity. A complex is considered active if it produces a % T/C of ≧125.

TABLE I

| | | | | | | | | | | IC 50 (mcg/ml)[a] | |
|---|---|---|---|---|---|---|---|---|---|---|---|
| Formula | Compound | $D_1$ | $D_2$ | A | $X_1$ | $X_2$ | n | Y | M | B 16 | HCT 116 |
| 2 | TNO 306 | P | P | $(CH_2)_2$ | — | — | 2 | Cl | Pd(II) | 57 | — |
| 3 | TNO 345 | P | P | $(CH_2)_2$ | — | — | 2 | $NO_3$ | Pd(II) | 4.0 | 19.6 |
| 4 | TNO 347 | P | P | $(CH_2)_2$ | $NO_3$ | — | 1 | $NO_3$ | Co(II) | 413 | >500 |
| 5 | TNO 354 | P | P | $(CH_2)_2$ | — | — | 2 | $NO_3$ | Ni(II) | 4.1 | 1.3 |
| 6 | TNO 357 | P | P | Cis-CH—CH | — | — | 2 | Cl | Pd(II) | 27.7 | 13.1 |
| 7 | TNO 376 | P | P | $(CH_2)_2$ | Br | — | 1 | Br | Pd(II) | 0.7 | 6.3 |
| 8 | TNO 396 | P | P | cis-CH—CH | Cl | Cl | 0 | — | Fe(II) | 452 | 383 |

[a]concentration which inhibits cell growth by 50%.

The results of testing the metal complexes are summarized in Table III which lists the maximum % T/C achieved by each complex and the dose producing that effect.

DRUG PREPARATION

For the in vitro cytotoxicity studies the drugs were dissolved or suspended, depending on their solubility, in 0.9% NaCl solution. Occasionally, 5% dextrose in water or 10% DMSO in 0.9% NaCl was used. The compounds were prepared for in vivo treatment by dissolving or suspending, with the addition of minimal amounts of Tween 80, in water.

bis(diphenylphosphino)ethane will be defined as diphos, 1-diphenylphosphino-2-diphenylarsinoethane as arphos and cis-1,2-bis(diphenylphosphino)ethylene as dppen.

Example 1

Bis[cis-1,2-bis(diphenylphosphino)ethylene]dichloro iron(II), having formula 8 (TNO 396) of the formula sheet.

A hot (~70° C.) filtered solution of anhydrous iron-(II) chloride (0.2536 g, 2 mmol) in 30 ml of ethanol was added to a boiling solution of dppen (1.584 g, 4 mmol) in 60 ml of ethanol. The resultant suspension was stirred for 1 hour at boiling temperature. After cooling to room

TABLE II

| Formula | Compound | $D_1$ | $D_2$ | A | $X_1$ | $X_2$ | n | Y | M | P 388 Maximum % T/C | Dose[a] |
|---|---|---|---|---|---|---|---|---|---|---|---|
| 9 | TNO 302 | P | P | $(CH_2)_2$ | — | — | 1 | Otf | Rh(I) | 153 | 4 |
| 2 | TNO 306 | P | P | $(CH_2)_2$ | — | — | 2 | Cl | Pd(II) | 144 | 60 |
| 10 | TNO 316 | P | P | $(CH_2)_2$ | — | — | 1 | $ClO_4$ | Rh(I) | 150 | 12.5 |
| 11 | TNO 342 | P | P | $(CH_2)_2$ | I | I | 0 | — | Pd(II) | 139 | 5 |
| 12 | TNO 343 | P | P | $(CH_2)_2$ | — | — | 2 | $ClO_4$ | Pd(II) | 178 | 200 |
| 13 | TNO 344 | P | P | $(CH_2)_2$ | — | — | 1 | $ClO_4$ | Ir(I) | 167 | 200 |
| 14 | TNO 346 | P | P | $(CH_2)_2$ | Br | — | 1 | Br | Co(II) | 167 | 100 |
| 4 | TNO 347 | P | P | $(CH_2)_2$ | $NO_3$ | — | 1 | $NO_3$ | Co(II) | 161 | 100 |
| 5 | TNO 354 | P | P | $(CH_2)_2$ | — | — | 2 | $NO_3$ | Ni(II) | 139 | 50 |
| 15 | TNO 355 | P | P | $(CH_2)_2$ | Cl | Cl | 1 | $ClO_4$ | Ph(III) | 167 | 100 |
| 16 | TNO 358 | P | P | $(CH_2)_2$ | — | — | 2 | $ClO_4$ | Co(II) | 144 | 100 |
| 17 | TNO 363 | P | P | $(CH_2)_2$ | Cl | Cl | 1 | Cl | Rh(III) | 133 | 50 |
| 18 | TNO 395 | P | As | $(CH_2)_2$ | Cl | Cl | 1 | $ClO_4$ | Rh(III) | 136 | 200 |
| 8 | TNO 396 | P | P | cis-CH=CH | Cl | Cl | 0 | — | Fe(II) | 150 | 200 |
| 19 | TNO 404 | P | P | $(CH_2)_2$ | — | — | 2 | $ClO_4$ | Ni(II) | 240 | 25 |
| 20 | TNO 405 | P | P | cis-CH=CH | Cl | Cl | 1 | $FeCl_4$(III) | Fe(III) | 160 | 100 |
| 21 | TNO 407 | P | As | $(CH_2)_2$ | — | — | 2 | $ClO_4$ | Co(II) | 130 | 200 |
| 22 | TNO 413 | P | P | $(CH_2)_2$ | 0 | 0 | 1 | $ClO_4$ | Ir(III) | 170 | 200 |

[a]dose is mg/kg administered ip, 1 ×on day 1.

TABLE IIa

| Formula | Compound | $D_1$ | $D_2$ | A | $X_1$ | $X_2$ | n | Y | M | L1210 Max. % T/C | Dose[a] | Li210/DDP[b] Max. % T/C | Dose[a] |
|---|---|---|---|---|---|---|---|---|---|---|---|---|---|
| 2 | TNO 306 | P | P | $(CH_2)_2$ | — | — | 2 | Cl | Pd(II) | 100 | 1.9 | 100 | 3.0 |
| 10 | TNO 316 | P | P | $(CH_2)_2$ | — | — | 1 | $ClO_4$ | Rh(I) | 133 | 160 | 157 | 120 |
| 3 | TNO 345 | P | P | $(CH_2)_2$ | — | — | 2 | $No_3$ | Pd(II) | 100 | 0,8 | NT[c] | — |
| 14 | TNO 346 | P | P | $(CH_2)_2$ | Br | — | 1 | Br | Co(II) | 100 | 200 | NT | — |
| 4 | TNO 347 | P | P | $(CH_2)_2$ | $NO_3$ | — | 1 | $NO_3$ | Co(II) | 100 | 100 | 150 | 50 |
| 5 | TNO 354 | P | P | $(CH_2)_2$ | — | — | 2 | $NO_3$ | Ni(II) | 100 | 80 | 138 | 80 |
| 15 | TNO 355 | P | P | $(CH_2)_2$ | Cl | Cl | 1 | $ClO_4$ | Rh(III) | 114 | 80 | 119 | 49 |
| 16 | TNO 358 | P | P | $(CH_2)_2$ | — | — | 2 | $ClO_4$ | Co(II) | 142 | 120 | 143 | 100 |

[a]dose is mg/kg administered ip, 7x on day 1.
[b]L1210/DDP test of an analog done concomitantly with the L1210 test of that analog
[c]NT is not tested

TABLE III

| Formula | Compound | $D_1$ | $D_2$ | A | $X_1$ | $X_2$ | n | Y | M | B 16 Maximum % T/C | Dose[a] |
|---|---|---|---|---|---|---|---|---|---|---|---|
| 9 | 302 | P | P | $(CH_2)_2$ | — | — | 1 | Otf | Rh(I) | 150/126[b] | 3.2 |
| 2 | TNO 306 | P | P | $(CH_2)_2$ | — | — | 2 | Cl | Pd(II) | 202/151 | 12 |
| 10 | TNO 316 | P | P | $(CH_2)_2$ | — | — | 1 | $ClO_4$ | Rh(I) | 131 | 16 |
| 12 | TNO 343 | P | P | $(CH_2)_2$ | — | — | 2 | $ClO_4$ | Pd(II) | 204 | 60 |
| 13 | TNO 344 | P | P | $(CH_2)_2$ | — | — | 1 | $ClO_4$ | Ir(I) | 150 | 20 |
| 4 | TNO 347 | P | P | $(CH_2)_2$ | $NO_3$ | — | 1 | $NO_3$ | Co(II) | 171 | 20 |
| 5 | TNO 354 | P | P | $(CH_2)_2$ | — | — | 2 | $NO_3$ | Ni(II) | 183 | 30 |
| 15 | TNO 355 | P | P | $(CH_2)_2$ | Cl | Cl | 1 | $ClO_4$ | Rh(III) | 171 | 30 |
| 16 | TNO 358 | P | P | $(CH_2)_2$ | — | — | 2 | $ClO_4$ | Co(II) | 150 | 20 |

[a]dose in mg/kg/inj. administered ip, gd 1–9.
[b]figures separated by slashes represent data generated in separate experiments.

EXAMPLES

The following examples illustrate the chemical preparation of the compounds in the compositions and methods of this invention and as such are not to be constructed as limiting the scope thereof. All the reactions are carried out in an atmosphere of dry nitrogen. 1,2- temperature the product was filtered off, washed with ethanol and ether and dried in vacuo at 50° C.
Yield: 1.74 g of a yellow solid (95.1 wt. %)
Melting point: 275°–278° C.
Analysis (wt. %):
Calculated: C 67.92; H 4.79; Cl 7.72;

Example 2

Bis[cis-1,2-bis(diphenylphosphino)ethylene]dichloro iron(III) tetrachloroferrate(III), having formula 20 (TNO 405) of the formula sheet.

A solution of iron(III) chloride (0.4866 g, 3.75 mmol) in 15 ml of methanol was added to a solution of dppen (1.485 g, 3.75 mmol) in a mixture of 15 ml of acetone and 15 ml of methanol at 70° C. The resultant green suspension was stirred for 1 hour at 70° C. and then cooled to room temperature. After standing overnight, the product was filtered off, washed with methanol, benzene and ether and dried in vacuo at 50° C.

Yield: 1.56 g of a green solid (93.4 wt.%)
Melting point: 200°–202° C.
Analysis (wt. %):
Calculated: C 55.89; H 3.94; Cl 19.05;
Found: C 56.79; H 4.23; Cl 18.86.

Example 3

Bis[1,2-bis(diphenylphosphino)ethane]bromo cobalt-(II) bromide, having formula 14 (TNO 346) of the formula sheet.

Co(II) bromide.hexahydrate (1.2 g, 3.673 mmol) in 10 ml of methanol was added to a suspension of diphos (3 g, 7.5376 mmol) in 50 ml of methanol. The resultant dark brown-green suspension was stirred for 1 hour at room temperature, followed by 0.5 hour at boiling temperature. The almost clear solution was filtered and evaporated. The residue was recrystallized from aqueous ethanol (1:3) and dried in vacuo at 60° C.

Yield: 2.65 g of a dark-green solid (71.6 wt. %)
Melting point: 120°–125° C.
Analysis (wt. %):
Calculated (+2EtOH): C 60.72; H 5.42; Cl 14.44;
Found: C 60.89; H 5.29; Cl 14.17;

Example 4

Bis[1,2-bis(diphenylphosphino)ethane]nitrato cobalt-(II) nitrate, having formula 4 (TNO 347) of the formula sheet.

A solution of Co(II) nitrate.hexahydrate (0.518 g, 2 mmol) in 20 ml of acetone was added dropwise with stirring to a suspension of diphos (1.99 g, 5 mmol) in 40 ml of acetone in 15 minutes. The resultant clear, brown solution was stirred at room temperature for 1 hour and then concentrated to 20 ml. About 100 ml of ether is added, the brown precipitate which formed is filtered off and washed with ether. The product was recrystallized from acetone and dried in vacuo at 60° C.

Yield: 1.21 g of a dark brown solid (62.1 wt. %)
Melting point: 138°–140° C.
Analysis (wt. %):
Calculated: C 63.16; H 4.96; N 2.83; O 10.53;
Found: C 63.42; H 5.46; N 2.56; O 10.65.

Example 5

Bis[1,2-bis(diphenylphosphino)ethane] cobalt(II) diperchlorate, having formula 16 (TNO 358) of the formula sheet.

A solution of cobalt(II) perchlorate.hexahydrate (1.5 g, 4.1 mmol) in 40 ml of acetone is added dropwise with stirring to a suspension of diphos (4.1 g, 10.3 mmol) in 80 ml of acetone in 15 minutes. The resultant yellow suspension is stirred for 1.5 hour at room temperature. Then the product was filtered off, washed with acetone and dried in vacuo at 100° C.

Yield: 4.25 g of a yellow solid (98.4 wt. %)
Melting point: 235°–240° C.
Analysis (wt. %):
Calculated: C 59.21; H 4.56; Cl 6.73;
Found: C 59.31; H 4.67; Cl 6.56.

Example 6

Bis[1-diphenylphosphino-2-diphenylarsinoethane]-cobalt(II) diperchlorate, having formula 21 (TNO 407) of the formula sheet.

The named product was prepared in a manner similar to the named product of example 5 from cobalt(II)perchlorate.hexahydrate (0.732 g, 2 mmol) and arphos (1.77 g, 4 mmol).

Yield: 0.53 g of a yellow solid (23.2 wt. %)
Melting point: ±225° C. (explosion).
Analysis (wt. %):
Calculated (+0.5 $H_2O$): C 54.23; H 4.29; Cl 6.16;
Found: C 54.19; H 4.26; Cl 6.13.

Example 7

Bis[1,2-bis(diphenylphosphino)ethane]rhodium(I) triflate, having formula 9 (TNO 302) of the formula sheet.

To a suspension of (cis,cis-1,5-cyclooctadiene)chloro rhodium(I) dimer (0.9856 g, 2 mmol) in 10 ml of acetone a solution of silver(I) triflate (1.02 g, 3,97 mmol) in 15 ml of acetone was added dropwise with stirring in 10 minutes. After 2 hours stirring in the dark, the formed silver(I) chloride was filtered off and washed with acetone. Then diphos (3.58 g, 9 mmol) was added to the filtrate by means of 15 ml of acetone and after 1 hour stirring at room temperature, the volume was reduced to 15 ml. 60 ml of ether were added dropwise and the resultant suspension was stored overnight at ±3° C. The product was filtered off, washed with ether and dried in vacuo.

Yield: 3.96 g of a yellow solid (95 wt. %)
Melting point: 225°–230° C.
Analysis (wt. %):
Calculated: C 60.69; H 4.58; S 3.06; F 5.44; P 11.83;
Found: C 60.49; H 4.73; S 2.93; F 5.31; P 10.99.

Example 8

Bis[1,2-bis(diphenylphosphino)ethane]rhodium(I) perchlorate, having formula 10 (TNO 316) of the formula sheet.

3.35 ml of acetylacetone (3.255 g, 32.55 mmol) were added to a suspension of (cis,cis-1,5-cyclooctadiene)-chloro rhodium(I) dimer (8.2 g, 16.27 mmol) in 90 ml of ether. The suspension was then cooled to −80° C. and a solution of potassiumhydroxide (5.478 g, 97.65 mmol) in 19 ml of water was added dropwise with stirring in 30 minutes. Stirring was continued without cooling untill room temperature was reached, followed by 4 hours at room temperature. Then 25 ml of water and 200 ml of benzene were added. Work-up of the organic layer yielded 8.4 g of a yellow solid (83.3 wt. %)=(cis,cis-1,5-cyclooctadiene) acetylacetonato rhodium(I).

To a solution of (cis,cis-1,5-cyclooctadiene)acetylacetonato rhodium(I) (0.626 g, 2.02 mmol) prepared as described above, and 70% perchloric acid (0.287 g, 2 mmol) in 15 ml of tetrahydrofuran was added diphos (1.67 g, 4.2 mmol) by means of 10 ml of tetrahydrofuran. The resultant suspension was stirred for 0.5 hour at room temperature and subsequently for 2 hours at boiling temperature. After cooling the volume was reduced to 10 ml, stored overnight at −20° C.

Found: C 68.00; H 4.99; Cl 7.71;

and then the product was filtered off, washed with ether, recrystallized from dichloromethane/tetrahydrofuran and dried in vacuo at 50° C.

Yield: 1.68 g of an orange-yellow solid (84 wt. %)
Melting point: 282° C.
Analysis (wt. %):
Calculated: C 62.51; H 4.81; Cl 3.55; O 6.41;
Found: C 62.43; H 4.83; Cl 3.57; O 6.22.

Example 9

Bis[1,2-bis(diphenylphosphino)ethane]dichloro rhodium(III) chloride, having formula 17 (TNO 363) of the formula sheet.

Diphos (3.016 g, 7.5756 mmol) was added in portions with stirring to a boiling solution of rhodium(III) chloride.trihydrate (0.8 g, 3.0388 mmol) in 65 ml of ethanol in 15 minutes. The resultant brown suspension was then stirred at boiling temperature for 3 hours. The almost clear solution was then treated with active coal and filtered hot; the volume was reduced to 15 ml and slow addition of ether and subsequent cooling to +3° C. afforded the product. This was filtered off, washed with ether and dried in vacuo.

Yield: 1.37 g of a yellow solid (44.9 wt. %)
Melting point: 265°-270° C.
Analysis (wt. %):
Calculated (+3 EtOH): C 60.88; H 5.77; Cl 9.30; O 4.20;
Found: C 60.64; H 5.68; Cl 9.06; O 3.68.

Example 10

Bis[1,2-bis(diphenylphosphino)ethane] dichloro rhodium(III) perchlorate, having formula 15 (TNO 355) of the formula sheet.

Sodium perchlorate.hydrate (1.07 g, 7.597 mmol) in 5 ml of water was added dropwise with stirring to a boiling solution of the named product of example 9 (1.527 g, 1.5194 mmol) in a mixture of 50 ml of ethanol and 25 ml of water in 10 minutes. The resultant suspension was kept overnight at +5° C.; the product was then filtered off, washed with ethanol and water, recrystallized from dichloromethane/tetrahydrofuran and dried in vacuo at 90° C.

Yield: 1.0 g of a yellow solid (61.7 wt. %)
Analysis (wt. %):
Calculated: C 58.36; H 4.49; Cl 9.95;
Found: C 58.15; H 5.13; Cl 9.75.

Example 11

Bis[1-diphenylphosphino-2-diphenylarsino] dichloro rhodium(III) chloride, having formula 23 (TNO 389) of the formula sheet.

The named product was prepared in a manner similar to the named product of example 9 from arphos (3.32 g, 7.5 mmol) and rhodium(III)chloride.trihydrate (0.79 g, 3.0 mmol), except that 15 hours of stirring at boiling temperature was needed.

Yield: 2.7 g of a yellow solid (82.3 wt. %)
Melting point: 265°-270° C. (decomposition).
Analysis (wt. %):
Calculated (+1.5 H₂O): C 55.71; H 4.59; Cl 9.49;
Found: C 55.67; H 4.54; Cl 9.04.

Example 12

Bis[1-diphenylphosphino-2-diphenylarsinoethane]dichloro rhodium(III) perchlorate, having formula 18 (TNO 395) of the formula sheet.

Sodiumperchlorate.hydrate (0.7 g, 5 mmol) in 5 ml of water was added dropwise with stirring to a boiling solution of the named product of example 11 (1.0 g, 0.914 mmol) in 100 ml of ethanol in 10 minutes. The resultant suspension was kept overnight at +5° C.; then the product was filtered off, washed thoroughly with water, then ethanol and ether and dried in vacuo.

Yield: 0.72 g of a dark-yellow solid (67.9 wt. %)
Melting point: >310° C. (decomposition)
Analysis (wt. %):
Calculated (+1 H₂O): C 53.11; H 4.29; Cl 9.04; O 6.80;
Found: C 52.90; H 4.42; Cl 8.57; O 6.42.

Example 13

Bis[1,2-bis(diphenylphosphino)ethane] iridium(I) perchlorate, having formula 13 (TNO 344) of the formula sheet.

Diphos (1.26 g, 3.16 g mmol) was added to a solution of (cis,cis-1,5-cyclooctadiene) chloro iridium(I) dimer (0.506 g, 0.754 mmol) in 10 ml of benzene. The resultant suspension was stirred at boiling temperature for 3 hours. After cooling to room temperature, the suspension was kept overnight at +6° C. The orange solid was then filtered off, washed with benzene and dissolved in 30 ml of ethanol. Sodiumperchlorate.hydrate (0.96 g, 6.838 mmol) was added, the resultant suspension was stirred for 3 hours at room temperature and kept overnight at −20° C. The product was filtered off, washed with ethanol and water, recrystallized from dichloromethane/ether and dried in vacuo at 100° C.

Yield: 1.12 g of an orange solid (68.7 wt. %)
Melting point: 215°-220° C.
Analysis (wt. %):
Calculated: C 57.37; H 4.41; Cl 3.26; O 5.88;
Found: C 57.50; H 4.73; Cl 3.28; O 6.09.

Example 14

Bis[1,2-bis(diphenylphosphino)ethane]peroxo iridium(III) perchlorate, having the formula 22 (TNO 413) of the formula sheet.

A solution of the named product of example 13 (2.44 g, 2.2468 mmol) in 25 ml of dichloromethane is stirred vigorously in the air for 1 hour. Then 75 ml of ethanol is added and the resultant solution is slowly evaporated to 10 ml. The precipitated product was filtered off, washed with ethanol and dried in vacuo at 80° C.

Yield: 1.9 g of a light-orange solid (75.7 wt. %)
Melting point: 230°-235° C. (decomposition)
Analysis (wt. %):
Calculated: C 55.73; H 4.29; Cl 3.17; O 8.57; P 11.08;
Found: C 55.79; H 4.46; Cl 3.16; O 8.84; P 10.97.

Example 15

Bis[1,2-bis(diphenylphosphino)ethane]nickel(II) dinitrate, having formula 5 (TNO 354) of the formula sheet.

Diphos (4.0 g, 10.05 mmol) was added to a solution of nickel(II) nitrate.hexahydrate (1.45 g, 4.99 mmol) in 50 ml of ethanol. The resultant suspension was stirred for 1 hour at room temperature, followed by 0.5 hour at boiling temperature. Then water was added to the boiling suspension untill most of the solid was dissolved, the solution was filtered hot and cooled to −20° C. The precipitated product was filtered off, washed with ethanol, recrystallized twice from aqueous ethanol and dried in vacuo at 90° C.

Yield: 1.0 g of an orange solid (20.5 wt. %)
Melting point: 217°-230° C.

Analysis (wt. %):
Calculated: C 63.76; H 4.91; N 2.91;
Found: C 63.33; H 5.03; N 2.79.

Example 16

Bis[1,2-bis(diphenylphosphino)ethane] nickel(II) perchlorate, having formula 19 (TNO 404) of the formula sheet.

A solution of nickel(II) perchlorate.hexahydrate (0.731 g, 2 mmol) in 20 ml of acetone is added dropwise with stirring to a suspension of diphos (1.633 g, 4.1 mmol) in 40 ml of acetone in 30 minutes. The resultant suspension is stirred for 3.5 hour at room temperature. Then the product was filtered off, washed with acetone and dried in vacuo.
Yield: 1.87 g of a yellow solid (88.6 wt. %)
Melting point: 248° C.
Analysis (wt. %):
Calculated: C 59.23; H 4.59; Cl 6.73;
Found: C 59.22; H 4.74; Cl 6.47.

Example 17

Bis[1,2-bis(diphenylphosphino)ethane]palladium(II) dichlorate, having formula 2 (TNO 306) of the formula sheet.

A suspension of bis(acetonitril)dichloro palladium(II) (1.17 g, 4.51 mmol) and diphos (1.83 g, 4.6 mmol) in 25 ml of benzene was stirred at boiling temperature for 3 hours. After cooling, the suspension was evaporated and the residue was recrystallized from dimethylformamide/ether. It was then dissoved in dimethylformamide at 80° C. and diphos (1.63 g, 4.095 mmol) was added. After 1 hour of stirring at room temperature ether was added, the precipitate was filtered off, washed with ether and recrystallized from dimethylformamide.
Yield: 2.06 g of a white solid (47 wt. %)
Melting point: 283°-300° C.
Analysis (wt. %):
Calculated: C 64.06; H 4.96; Cl 7.27;
Found: C 63.7; H 5.0; Cl 6.91.

Example 18

Bis[1,2-(diphenylphosphino)ethane]diiodo palladium-(II) having formula 11 (TNO 342) of the formula sheet.

A solution of the named product of example 17 (1.46 g, 1.5 mmol) in a mixture of 25 ml of ethanol and 5 ml of water was added dropwise with stirring to a solution of sodium iodide (7.495 g, 50 mmol) in 20 ml of water in 10 minutes. The resultant suspension was stirred for 1 hour at room temperature, then the product was filtered off, washed with water and subsequently boiled in 300 ml of water/ethanol (1:1) for 0.5 hour; after cooling, the suspension was kept overnight at +3° C.; the product was filtered off, washed with water, ethanol and ether and dried in vacuo at 100° C.
Yield: 1.22 g of a light-yellow solid (70.5 wt. %)
Melting point: 281.5°-284.5° C.
Analysis (wt. %):
Calculated: C 53.97; H 4.15; I 21.95;
Found: C 53.32; H 4.21; I 21,29.

Example 19

Bis[1,2-bis(diphenylphosphino)ethane]palladium(II) diperchlorate, having formula 12 (TNO 343) of the formula sheet.

To a solution of perchloric acid (1.44 g, 10 mmol) in 25 ml of water was added dropwise with stirring a solution of the named compound of example 17 (0.97 g, 1 mmol) in a mixture of 20 ml of ethanol and 5 ml of water in 10 minutes. The resultant suspension was stirred at room temperature for 2 hours. The product was filtered off, washed with water and dried in vacuo at 100° C.
Yield: 0.83 g of a white solid (75 wt. %)
Melting point: 328°-333° C. (decomposition)
Analysis (wt. %):
Calculated (+1H$_2$O): C 55.75; H 4.47; Cl 6.33;
Found: C 55.5; H 4.7; Cl 6.3.

Example 20

Bis[1,2-bis(diphenylphosphino)ethane]palladium(II) dinitrate, having formula 3 (TNO 345) of the formula sheet.

A solution of potassiumnitrate (1.26 g, 2.59 mmol) in 5 ml of water was added dropwise with stirring to a solution of the named product of example 17 (1.2 g, 1.23 mmol) in 50 ml of warm water in about 2 minutes. The resultant suspension was stirred for 2 hours at room temperature. Then the product was filtered off, washed with water and and dried in vacuo at 100° C.
Yield: 0.75 g of a white solid (59.5 wt. %)
Melting point: 270°-280° C. (decomposition)
Analysis (wt. %):
Calculated: C 60.80; H 4.68; N 2.73; O 9.35;
Found: C 60.56; H 4.57; N 2.47; O 9.11.

Example 21

Bis[1,2-bis(diphenylphosphino)ethane]bromo palladium(II) bromide, having formula 7 (TNO 376) of the formula sheet.

Diphos (2.0 g, 5.025 mmol) was boiled under reflux with palladium(II) chloride (0.455 g, 2.566 mmol) in 50 ml of ethanol for 10 minutes. Then the resultant solution was cooled and added dropwise with stirring to an excess of aqueous sodium bromide in 15 minutes. The resultant suspension was stirred for 1 hour at room temperature, then the product was filtered off, washed with water, recrystallized from aqueous ethanol and dried in vacuo.
Yield: 1.30 g of a very light-yellow solid (48.2 wt. %)
Melting point: about 240° C. (decomposition)
Analysis (wt. %):
Calculated: C 58.26; H 4.61; Br 14.91;
Found: C 58.32; H 4.75; Br 14.61.

Example 22

Bis[cis-1,2-bis(diphenylphosphino)ethylene]palladium(II) dichloride, having formula 6 (TNO 357) of the formula sheet.

Dppen (1.584 g, 4 mmol) was boiled under reflux with palladium(II)chloride (0.3546 g. 2 mmol) in 50 ml of ethanol for 0.5 hour. The resultant, almost clear, solution filtered and the volume reduced to 15 ml. This solution was kept overnight at −20° C. and the crystallized product was filtered off, washed with ethanol and ether and dried in vacuo at 90° C.
Yield: 0.65 g of a cream solid (33.7 wt. %)
Melting point: >320° C. (decomposition)
Analysis (wt. %):
Calculated (+2H$_2$O): C 62.07; H 4.78; Cl 7.05;
Found: C 62.43; H 4.73; Cl 7.05.

Example 23

For the in vitro cytotoxicity studies the compounds were dissolved or suspended, depending on their solubility, in 0.9% NaCl solution. Occasionally, 5% dextrose in water or 10% DMSO in 0.9% NaCl was used. The compounds were prepared for in vivo treatment by dissolving or suspending, with the addition of minimal amounts of Tween 80, in water.

We claim:

1. A pharmaceutical composition comprising an effective tumor cell growth-inhibiting amount of a pharmaceutically active ingredient which further comprises a compound of the formula:

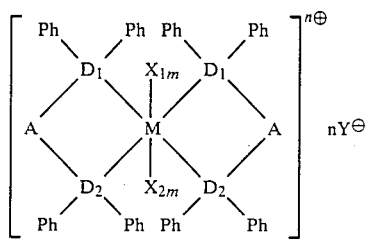

wherein
D₁ and D₂ are independently selected from the group consisting of phosphorous and arsenic;
A is independently selected from the group consisting of (CH₂)₂, (CH₂)₃ and cis-CH═CH;
(X₁)$_m$ and (X₂)$_m$ are halo or nitrato or (X₁)$_m$+(X₂)$_m$ form a peroxo linkage;
(Y)$_n$ is independently selected from the group consisting of halide, nitrate, pechlorate, triflate, and tetrahaloferrate (III);
m is 0 or 1;
n is 0, 1 or 2;
M is independently selected from the group consisting of Fe(II), Fe(III), Co(II), Rh(I), Rh(III), Ir(I), Ir(III), Ni(II), and Pd(II); and
Ph is phenyl and an inert, pharmaceutically acceptable carrier or diluent;
wherein said composition is useful for inhibiting the growth of animal tumor cells sensitive to the active ingredient, and wherein the active ingredient is a compound of the above-mentioned formula.

2. A method of treating tumor cells by administering tumor cell growth-inhibiting amounts of a compound of claim 1.

3. A composition according to claim 1 in which the composition is in dosage unit form for parenteral administration.

4. The composition according to claim 1, wherein said pharmaceutically active ingredient comprises a compound wherein M represents Pd(II) and m=0, n=2, and Y=chloride, each A═CH₂CH₂—, and D₁ and D₂ both represent phosphorus.

5. The composition according to claim 1, wherein said pharmaceutically active ingredient comprises a compound wherein M is Fe(II), m=1, X₁ and X₂ both are chloride, each A represents cis-CH═CH₂ D₁ and D₄ each represents phosphorous, m=0 and therefore Y is not present.

6. The composition according to claim 1, said compound having the formula:

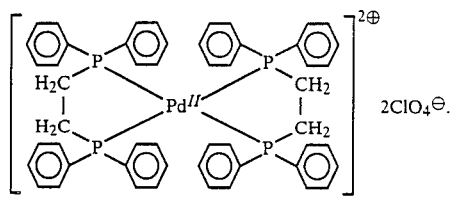

7. The composition according to claim 1, wherein said compound has the formula:

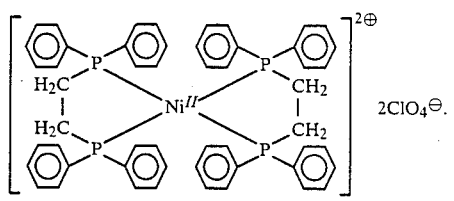

8. The composition having the formula:

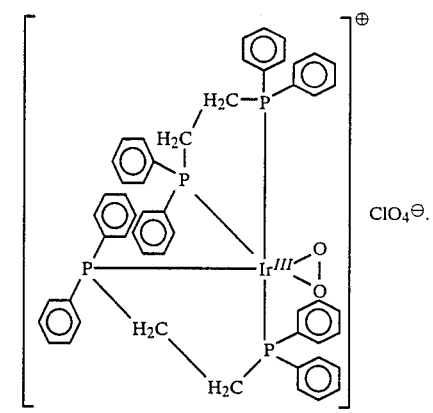

9. The composition having the formula:

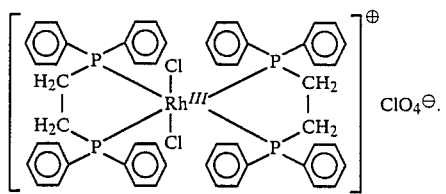

10. The compound having the formula:

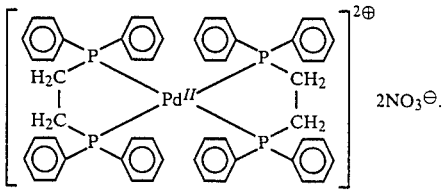

11. The compound having the formula:

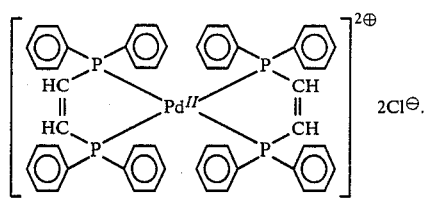
12. The compound having the formula:
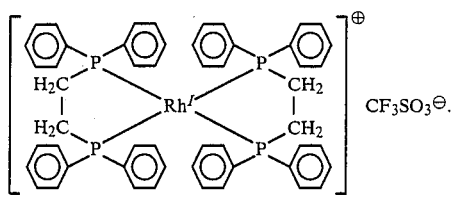
13. The compound having the formula:
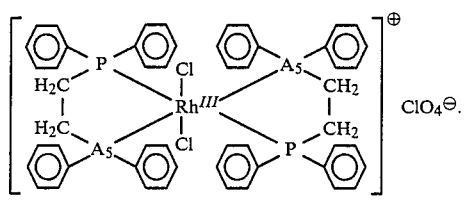
14. The compound having the formula:
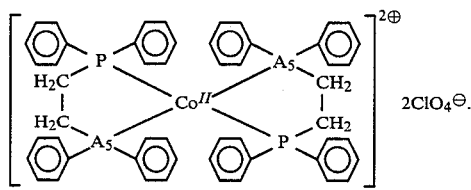
15. The compound having the formula:
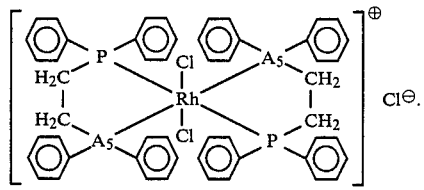
16. The composition according to claim 15, wherein said pharmaceutically active ingredient comprises a compound having the formula:
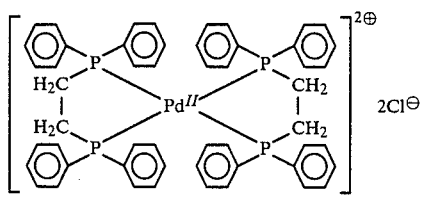
-continued
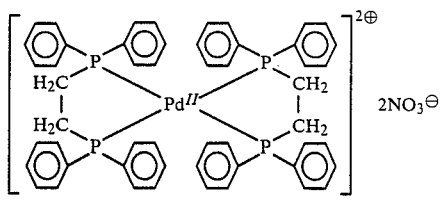
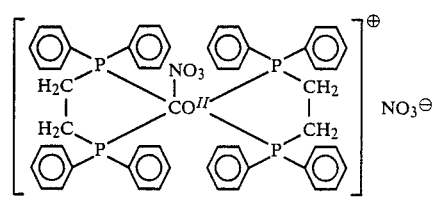
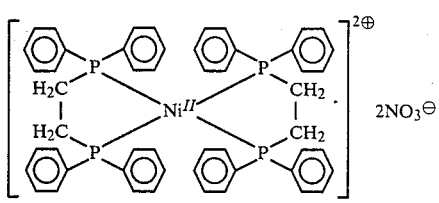
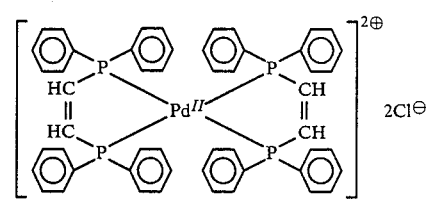
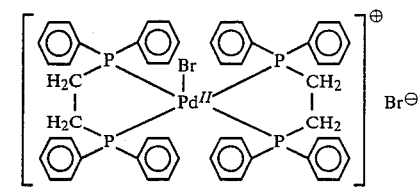
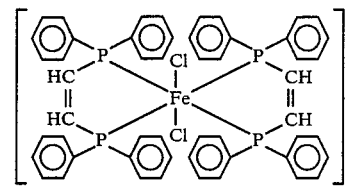
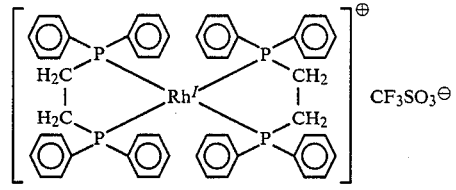
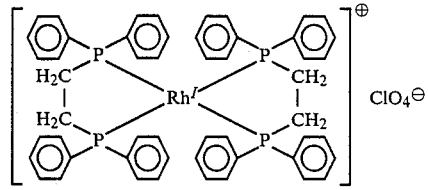

-continued
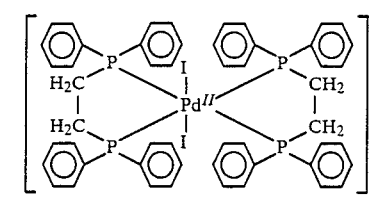
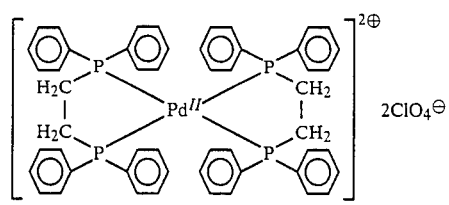
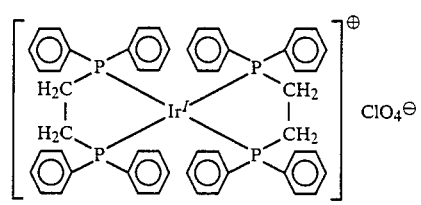
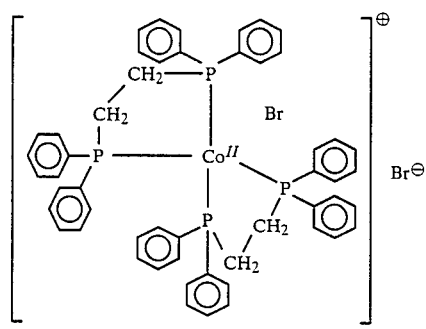
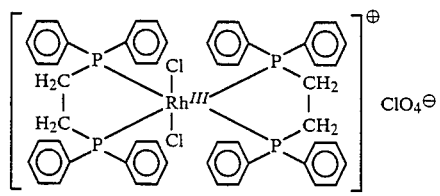
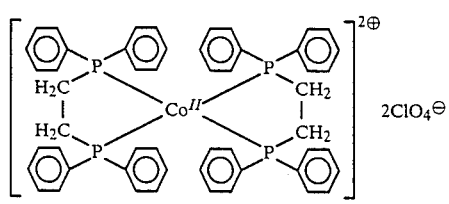
-continued
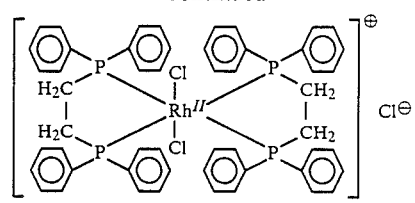
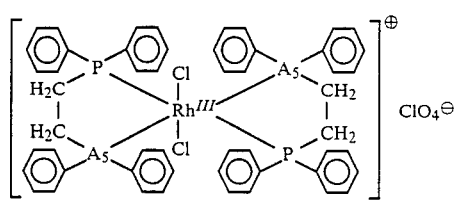
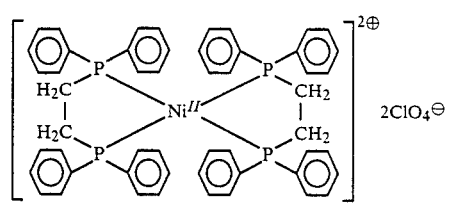
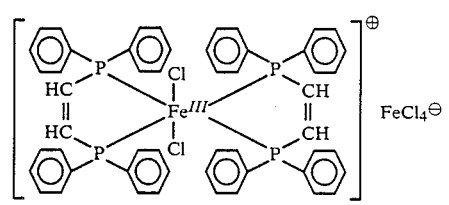
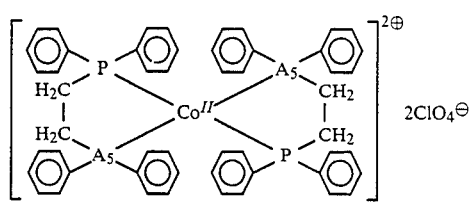
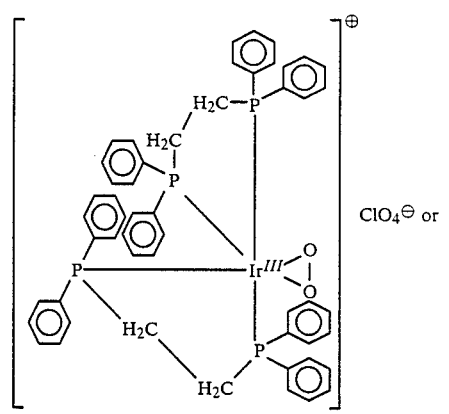
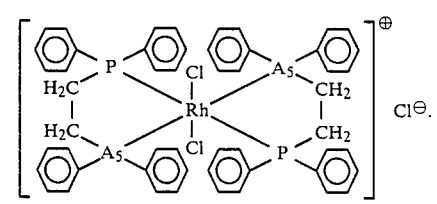
* * * * *